(12) United States Patent
Masumura

(10) Patent No.: US 9,638,641 B2
(45) Date of Patent: May 2, 2017

(54) INSPECTION SYSTEM AND INSPECTION ILLUMINATION DEVICE

(71) Applicant: CCS Inc., Kyoto-shi, Kyoto (JP)

(72) Inventor: Shigeki Masumura, Kyoto (JP)

(73) Assignee: CCS Inc., Kyoto-shi (JP)

( * ) Notice: Subject to any disclaimer, the term of this patent is extended or adjusted under 35 U.S.C. 154(b) by 0 days.

(21) Appl. No.: 14/649,200

(22) PCT Filed: Nov. 25, 2013

(86) PCT No.: PCT/JP2013/081658
§ 371 (c)(1),
(2) Date: Jun. 2, 2015

(87) PCT Pub. No.: WO2014/087868
PCT Pub. Date: Jun. 12, 2014

(65) Prior Publication Data
US 2015/0316488 A1    Nov. 5, 2015

(30) Foreign Application Priority Data

Dec. 3, 2012    (JP) .................................. 2012-264599

(51) Int. Cl.
*G01N 21/00*    (2006.01)
*G01N 21/88*    (2006.01)
(Continued)

(52) U.S. Cl.
CPC ..... *G01N 21/8806* (2013.01); *G01N 21/9501* (2013.01); *G01N 21/956* (2013.01); *G01N 2021/8822* (2013.01)

(58) Field of Classification Search
CPC .. C23C 16/18; H01S 3/10; H01J 61/20; H01J 61/00; H01J 35/20; H05G 2/003; H05G 2/00; H05H 1/24
(Continued)

(56) References Cited

U.S. PATENT DOCUMENTS

| 7,161,671 | B2 * | 1/2007 | Shibata | ............ | G01N 21/95607 |
| | | | | | 250/559.42 |
| 8,040,511 | B1 * | 10/2011 | Krishnan | ............... | G01B 11/26 |
| | | | | | 356/369 |
| 2007/0070336 | A1 * | 3/2007 | Maeda | ............... | G01N 21/8806 |
| | | | | | 356/237.2 |

FOREIGN PATENT DOCUMENTS

| JP | 63042453 A | 2/1988 |
| JP | 06180221 A | 6/1994 |

(Continued)

OTHER PUBLICATIONS

ISA Japanese Patent Office, International Search Report Issued in Patent Application No. PCT/JP2013/081658, Jan. 28, 2014, WIPO, 4 pages.

*Primary Examiner* — Tarifur Chowdhury
*Assistant Examiner* — Isiaka Akanbi
(74) *Attorney, Agent, or Firm* — Alleman Hall McCoy Russell & Tuttle LLP

(57) ABSTRACT

In order to provide an inspection illumination device that makes it possible to greatly change a light amount within an observation solid angle of an imaging device even in a case where a change in reflection or scattering taking place at a feature point is subtle, and thus detect such a minute feature point, the inspection illumination device includes: a surface light source that emits inspection light; a lens that is arranged between the surface light source and an inspection object, and provides an image of the surface light source near the inspection object; and a first light shielding mask that is arranged between the surface light source and the inspection object, and forms a dark domain within an illumination solid angle of the inspection light applied to each point on the inspection object.

8 Claims, 11 Drawing Sheets

(51) Int. Cl.
  *G01N 21/95* (2006.01)
  *G01N 21/956* (2006.01)
(58) Field of Classification Search
  USPC .......................................... 356/237.2–237.6
  See application file for complete search history.

(56) References Cited

FOREIGN PATENT DOCUMENTS

| | | | |
|---|---|---|---|
| JP | 08162511 | A | 6/1996 |
| JP | 11023243 | A | 1/1999 |
| JP | 2004101406 | A | 4/2004 |
| JP | 2008175583 | A | 7/2008 |
| JP | 2010261839 | A | 11/2010 |

* cited by examiner

FIG. 5(a)

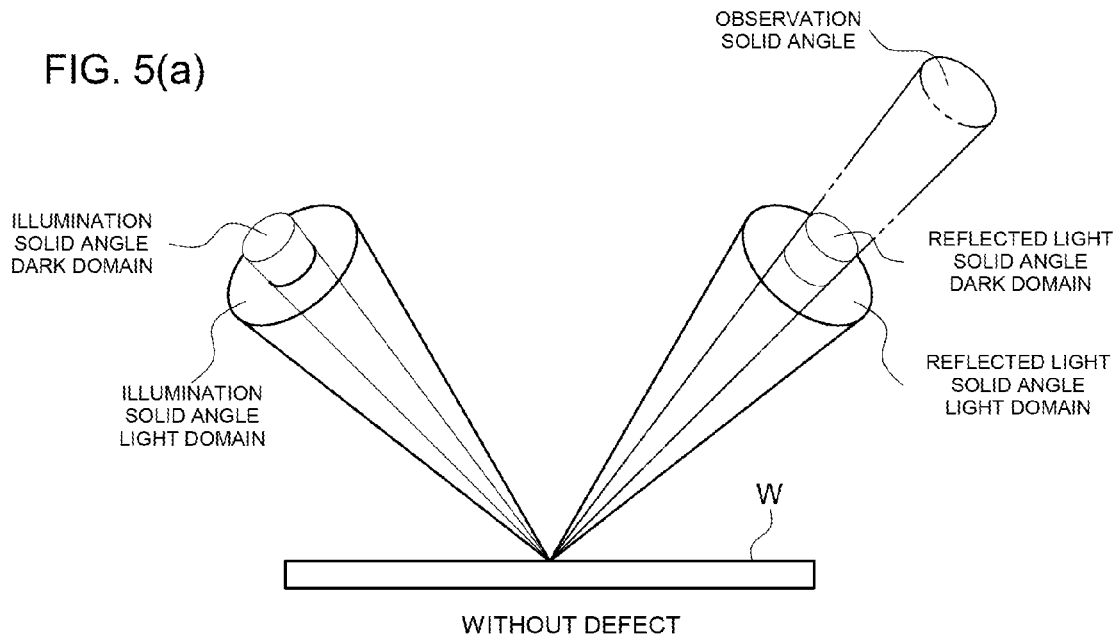

WITHOUT DEFECT

A DARK PICTURE IMAGE IS TAKEN WHEN NO DEFECT IS PRESENT
BECAUSE SETTEING IS PERFORMED SUCH THAT THE SIZE OF THE OBSERVATION SOLID ANGLE AND
THE SIZE OF THE REFLECTED LIGHT SOLID ANGLE DARK DOMAIN SUBSTANTIALLY COINCIDE WITH EACH OTHER.

FIG. 5(b)

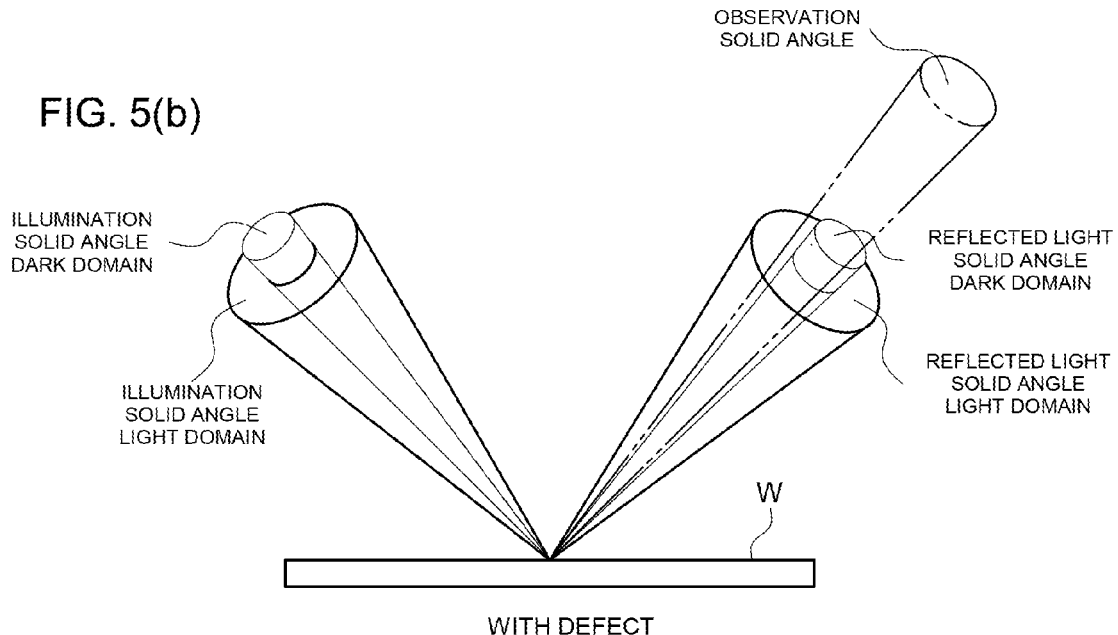

WITH DEFECT

IN THE CASE WHERE A REFLECTION DIRECTION IS CHANGED EVEN SUBTLY BECAUSE OF THE PRESENCE OF A DEFECT,
THE REFLECTED LIGHT SOLID ANGLE LIGHT DOMAIN MOVES INTO THE OBSERVATION SOLID ANGLE,
AND A LIGHT PICTURE IMAGE IS TAKEN.
DIFFERENCE IN BRIGHTNESS GREATLY APPEARS, AND THEREFORE EVEN A SMALL DEFECT CAN BE EASILY FOUND.

EVEN IN THE CASE WHERE A REFLECTION DIRECTION IS CHANGED EVEN SUBTLY BECAUSE OF THE PRESENCE OF A DEFECT, NO CHANGE OCCURS IN THE AMOUNT OF LIGHT DETECTED WITHIN THE OBSERVATION SOLID ANGLE. DIFFERENCE IN BRIGHTNESS DOES NOT APPEAR, AND THEREFORE A SMALL DEFECT CANNOT BE FOUND.

OSA  : OBSERVATION SOLID ANGLE
RSA1 : REFLECTED LIGHT SOLID ANGLE
       LIGHT DOMAIN
RSA2 : REFLECTED LIGHT SOLID ANGLE
       DARK DOMAIN

OSA : OBSERVATION SOLID ANGLE
RSA1 : REFLECTED LIGHT SOLID ANGLE LIGHT DOMAIN
RSA2 : REFLECTED LIGHT SOLID ANGLE DARK DOMAIN

INSPECTION SYSTEM AND INSPECTION ILLUMINATION DEVICE

TECHNICAL FIELD

The present invention relates to an inspection system and an inspection illumination device, both of which are used for, for example, illuminating an inspection object with inspection light to inspect an appearance, flaws, defects, and the like, of a product.

BACKGROUND ART

Examples of an inspection illumination device used for inspection of the appearance and the like of products include, as described in Patent Literature 1, coaxial illumination that makes an imaging direction and a direction in which an inspection object is illuminated coincide with each other. With coaxial illumination, included is: a light source that emits inspection light in a horizontal direction; and a half mirror that is arranged at an angle between the inspection object and an imaging device arranged above the inspection object; wherein the half mirror is configured so as to reflect the inspection light toward the inspection object as well as transmit reflected light from the inspection object toward the imaging device side.

Meanwhile, an ability to detect feature points such as defects from an imaged picture image that are difficult to detect even using an inspection illumination device as described above, has been demanded in recent years. More specifically, there are cases where inspection is difficult, such as a case where the shape of a product as an inspection object is special or complicated, and therefore it is difficult to apply inspection light at a sufficient intensity or with a sufficient light amount, and a case where even if inspection light can be applied, a reflected light amount from parts other than a part to be inspected is too large, or a feature point such as a defect is too small or subtle, and therefore contrast is unlikely to appear.

For example, it may be possible to increase inspection accuracy by limiting an illumination range of inspection light to only an inspection object using a diaphragm or the like, and thereby reducing stray light including reflected light and scattered light from objects other than the inspection object.

However, even if stray light entering an imaging device can be reduced by such a method, a very minute defect or the like may not produce a change in the brightness of an imaged picture image, and may not be detectable as a defect.

More specifically, even if a reflection direction of the applied inspection light is subtly changed by a minute defect or the like on an inspection object, in the case where the change is small enough to fall within an observation solid angle of an imaging device, no change is produced in the brightness of an imaged picture image, regardless of the presence or absence of a defect. Accordingly, such a minute defect or the like cannot be detected as machine vision.

CITATION LIST

Patent Literature

Patent Literature 1: Japanese Unexamined Patent Publication JP-A2010-261839

SUMMARY OF INVENTION

Technical Problem

The present invention is made in consideration of the problem as described above, and intends to provide an inspection system and an inspection illumination device, both of which for example, even in the case where illumination conditions are stringent, or a feature point such as a defect is very small and a change in reflection or scattering taking place at the feature point is subtle, make it possible to greatly change a light amount within an observation solid angle of an imaging device, and thus detect such a minute feature point.

Solution to Problem

That is, the present invention is made on the basis of a new idea that even in the case where a defect or the like on an inspection object is minute, and the amount of change in reflection or scattering due to the defect or the like is very subtle, the amount of change can be detected as a change within an observation solid angle of an imaging device by making it possible to adjust aspects such as the size or shape of an illumination solid angle of inspection light emitted from an inspection illumination device.

More specifically, the inspection system of the present invention is an inspection system including: an inspection illumination device that applies inspection light to an inspection object; and an imaging device that images light reflected or scattered at the inspection object, in which the inspection illumination device includes: a surface light source that emits the inspection light; a lens that is arranged between the surface light source and the inspection object, and provides an image of the surface light source near the inspection object; and a first light shielding mask that is arranged between the surface light source and the inspection object, and forms a dark domain within an illumination solid angle of the inspection light applied to each point on the inspection object; and the imaging device has an observation solid angle, wherein a shape or a size of the observation solid angle is set on the basis of a shape or a size of a dark domain within the illumination solid angle of the inspection light applied from the inspection illumination device to each point on the inspection object.

Also, the inspection illumination device of the present invention includes: a surface light source that emits inspection light; a lens that is arranged between the surface light source and an inspection object, and provides an image of the surface light source near the inspection object; and a first light shielding mask that is arranged between the surface light source and the inspection object, and forms a dark domain within an illumination solid angle of the inspection light applied to each point on the inspection object.

Since the image of the surface light source is provided near the inspection object by the lens, such an inspection system and inspection illumination device can apply the inspection light over the entire area without forming a shadow on the inspection object while forming a dark domain within an illumination solid angle of the inspection light through the first light shielding mask. Also, the sizes of illumination solid angles of the inspection light at respective points on the inspection object, and the sizes of dark domains can be made substantially uniform.

In other words, for example, in the case of converting the inspection light to parallel light through the lens, a part where the light is shielded by the first light shielding mask is formed as a shadow on the inspection object, whereas the present invention is adapted to be able to apply the inspection light only from a predetermined domain for an illumination solid angle of the inspection light at each point while applying the inspection light to each point without forming a shadow on the inspection object.

Further, since the first light shielding mask forms the dark domain in a part of the illumination solid angle of the inspection light applied to each point on the inspection object, and the observation solid angle is set in accordance with the size or shape of the dark domain, even in the case where a reflection direction or a scattering direction is subtly changed by a minute defect or the like, a ratio between a light domain and a dark domain can be easily changed within the observation solid angle of the imaging device, and therefore the minute defect or the like can be easily detected as a defect.

Also, various modal illumination solid angles can be formed, such as an illumination solid angle at each point on an inspection object, which has a dark domain only in the central part and a light domain only in the outer part, and therefore the inspection light can be applied at an illumination solid angle suitable for an inspection object.

In order to detect a change in a reflected light solid angle produced when a reflection direction of the inspection light is changed by a defect or the like even in the case where the change is very subtle, it is only necessary that the size of the observation solid angle is set substantially equal to the size of the dark domain of the illumination solid angle. In doing so, normally, a dark domain of a reflected light solid angle and the observation solid angle coincide with each other and a dark picture image is taken, whereas in the case where a reflection direction is changed even a little, a light domain of the reflected light solid angle moves into the observation solid angle, and thereby the change can be detected. Accordingly, even a minute defect or the like that has been undetectable in the past can be detected as contrast through machine vision.

In order to make it possible to control the sizes of illumination solid angles of the inspection light applied to respective points on the inspection object to be uniform, and freely adjust a tilt distribution of the illumination solid angles, it is only necessary to further include the first diaphragm that is arranged at a predetermined position with respect to a focal point of the lens. That is, by changing a stopping level of the first diaphragm, the sizes of illumination solid angles at respective points can be set to a desired size uniformly. Also, in the case of arranging the first diaphragm on the inner side of the focal point of the lens, the illumination solid angle of the inspection light applied to an outer side of an imaging plane, and the dark domain of the illumination solid angle can be tilted from the outer side toward a center side where a light axis is present. Further in the case of arranging the first diaphragm at the focal point of the lens, directions of illumination solid angles of the inspection light can be all made parallel to the light axis. In addition, in the case of arranging the first diaphragm on the outer side of the focal point of the lens, the illumination solid angle of the inspection light applied to the outer side of the imaging plane, and the dark domain of the illumination solid angle can be tilted from the center side where the light axis is present to the outer side. As described, the illumination solid angle and the dark domain of the illumination solid angle can be variously adjusted on the basis of the arrangement of the first diaphragm and the stopping level of the first diaphragm, and therefore a configuration suitable for an inspection object can be taken.

In order to make it easy to adjust the size or shape of the dark domain within the illumination solid angle of the inspection light applied to each point on the inspection object to a desired size or shape as well as prevent a shadow from being formed on the inspection object, it is only necessary that the first light shielding mask is arranged near the first diaphragm, and a light shielding part of the first light shielding mask is formed to be smaller than an aperture size of the first diaphragm.

In order to make it possible to easily inspect the shape accuracy of the inspection object as well, it is only necessary that a second light shielding mask formed with a predetermined mask pattern is arranged near an emission side of the surface light source. In doing so, a shadow not formed by the first light shielding mask can be formed on the inspection object by the second light shielding mask to form the pattern. Further, in the case where the shape of the inspection object has a problem, distortion occurs in the pattern, and therefore the defective shape can be easily detected.

Even in the case where coaxial illumination cannot be used, and inspection light must be applied from an obliquely upper side of an inspection object, in order to make it possible to provide an image of the entire surface of a surface light source on the inspection object, and make illumination solid angles at respective points uniform to make measurement accuracy constant over an entire inspection object plane, it is necessary that the surface light source has a light emitting plane; a light axis of the lens is arranged obliquely to the inspection object plane on the inspection object; and a first virtual plane including the light emitting plane, a second virtual plane including a principal plane of the lens, and a third virtual plane including the inspection object plane intersect on one straight line.

In the case where an inspection object has an inspection object curved surface, in order to provide the image the surface light source over the entire curved surface to increase defect detection accuracy on the curved surface, it is only necessary that the surface light source have a light emitting curved surface; and a shape of the light emitting curved surface is set such that an image of the light emitted from each point on the light emitting curved surface is provided at each point on the inspection object curved surface.

Advantageous Effects of Invention

The inspection system and inspection illumination device of the present invention make it possible to freely adjust the sizes or configurations of an illumination solid angle and a dark domain of the illumination solid angle of inspection light applied to each point on an inspection object, and therefore detect even a minute defect or the like that has been difficult to detect in the past.

BRIEF DESCRIPTION OF DRAWINGS

FIGS. 5(a) and 5(b) are schematic diagrams illustrating a defect detection principle in the same embodiment.

REFERENCE CHARACTER LIST

Figure 1:
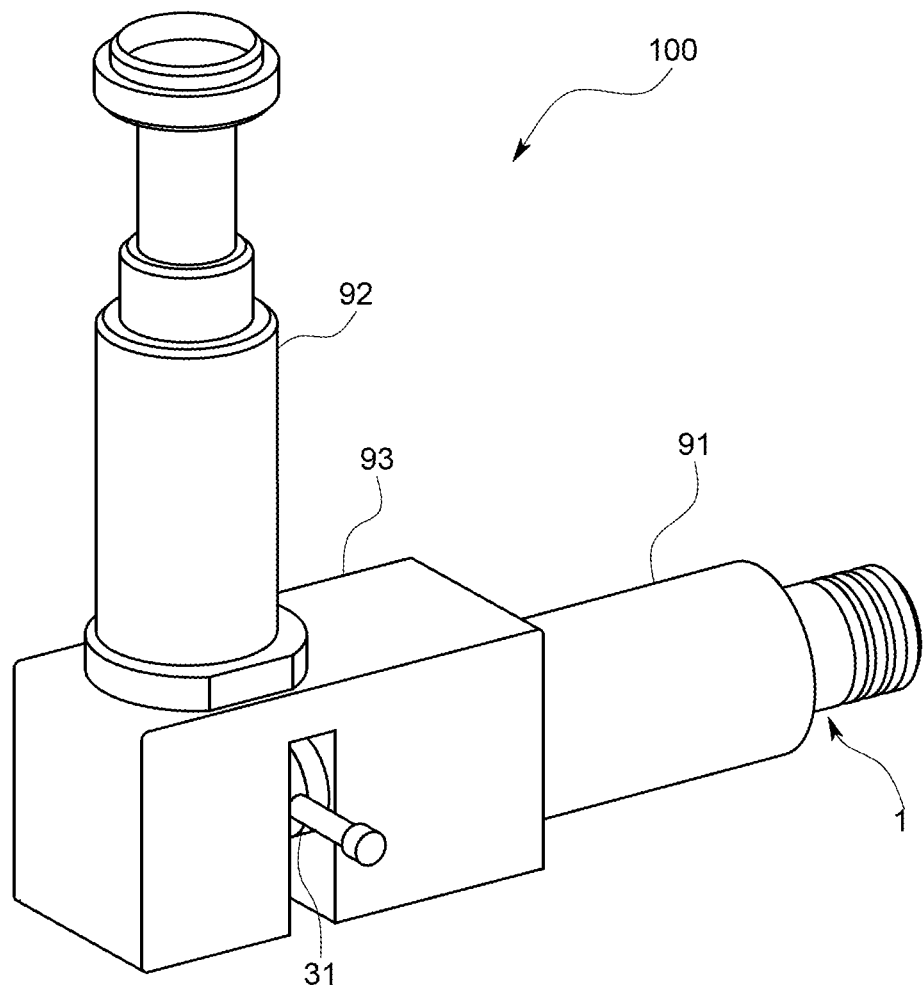
FIG. 1 is a schematic perspective view illustrating the appearance of an inspection system according to one embodiment of the present invention.

200: Inspection system
100: Inspection illumination device
1: Surface light source
11: Light emitting surface
12: Radiation fin
2: Lens
31: First diaphragm
32: Second diaphragm
33: Third diaphragm
34: Fourth diaphragm
4: Half mirror
41: Frame body
91: First tubular body
92: Second tubular body
93: Box body
C: Imaging device
IM: Imaging plane
L1: Illumination light path
L11: First light path
L12: Second light path
L2: Reflection light path
M1: First light shielding mask
M2: Second light shielding mask
W: Inspection object

DESCRIPTION OF EMBODIMENTS

A first embodiment of the present invention is described.

An inspection system 200 configured to include an inspection illumination device 100 of the first embodiment and an imaging device C uses so-called coaxial illumination in which a direction to image an inspection object W and a direction to illuminate the inspection object W coincide with each other, and is used to make a defect on the inspection object W appear as contrast in a picture image imaged by the imaging device C. Note that feature points on the inspection object W, such as defects, include, for example, a surface flaw, an external shape, wide-ranging problems such as the presence or absence of a hole, and other features.

Figure 2:
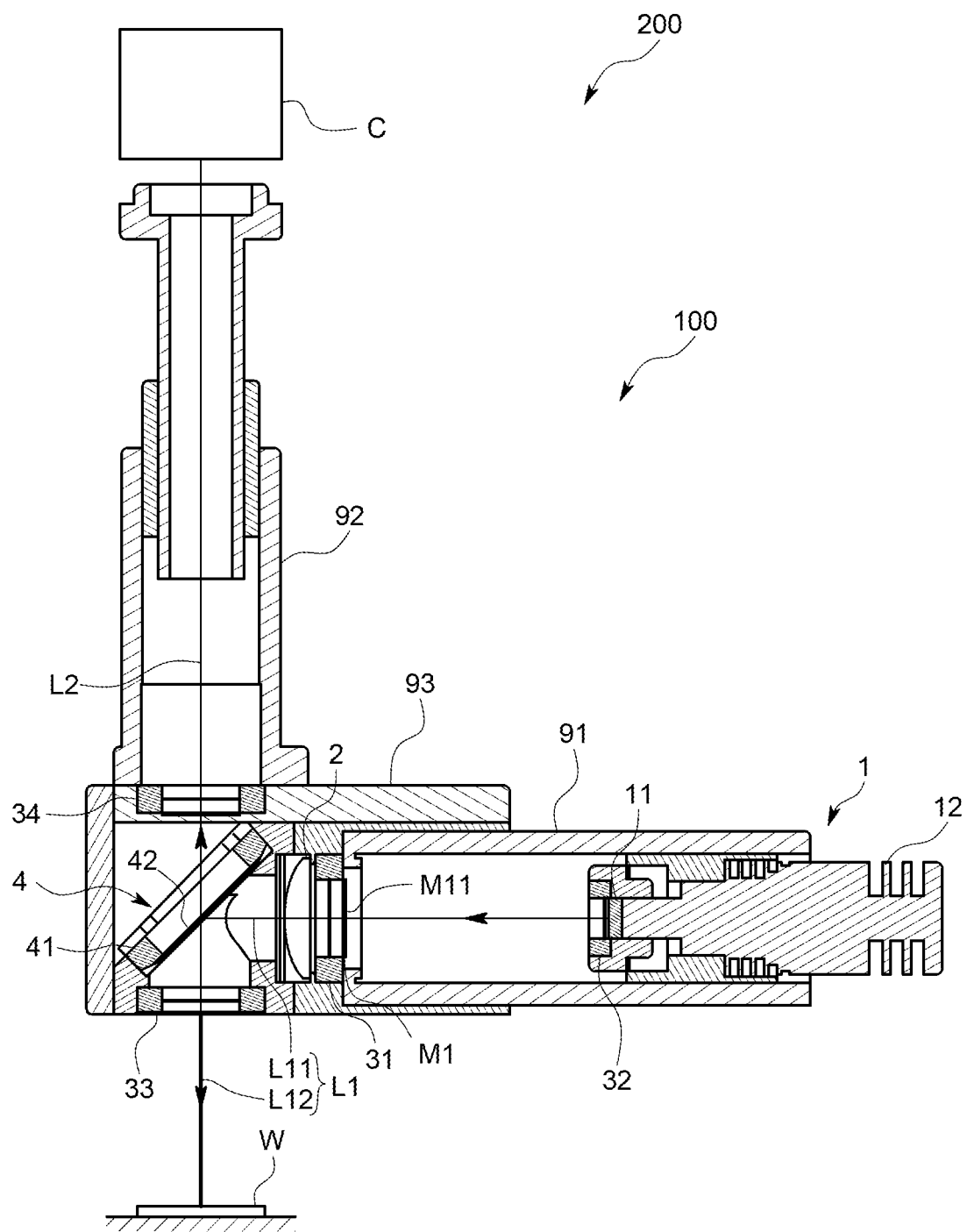
FIG. 2 is a schematic cross-sectional view illustrating the internal structure of the inspection system in the same embodiment.

The inspection illumination device 100, as illustrated in a perspective view of FIG. 1 and in a cross-sectional view of FIG. 2, has a substantially L-shaped housing, inside which an illumination light path L1 through which inspection light is applied from a surface light source 1 to the inspection object W and a reflection light path L2 through which reflected light from the inspection object W reaches the imaging device C are formed. More specifically, a first tubular body 91 extending in a horizontal direction, and a second tubular body 92 extending in a vertical direction are respectively connected to a box body 93, and on an upper surface opening side of the second tubular body 92 extending in the vertical direction, the imaging device C is attached, whereas on a lower surface opening of the box body 93, the inspection object W is placed.

Figure 3A:
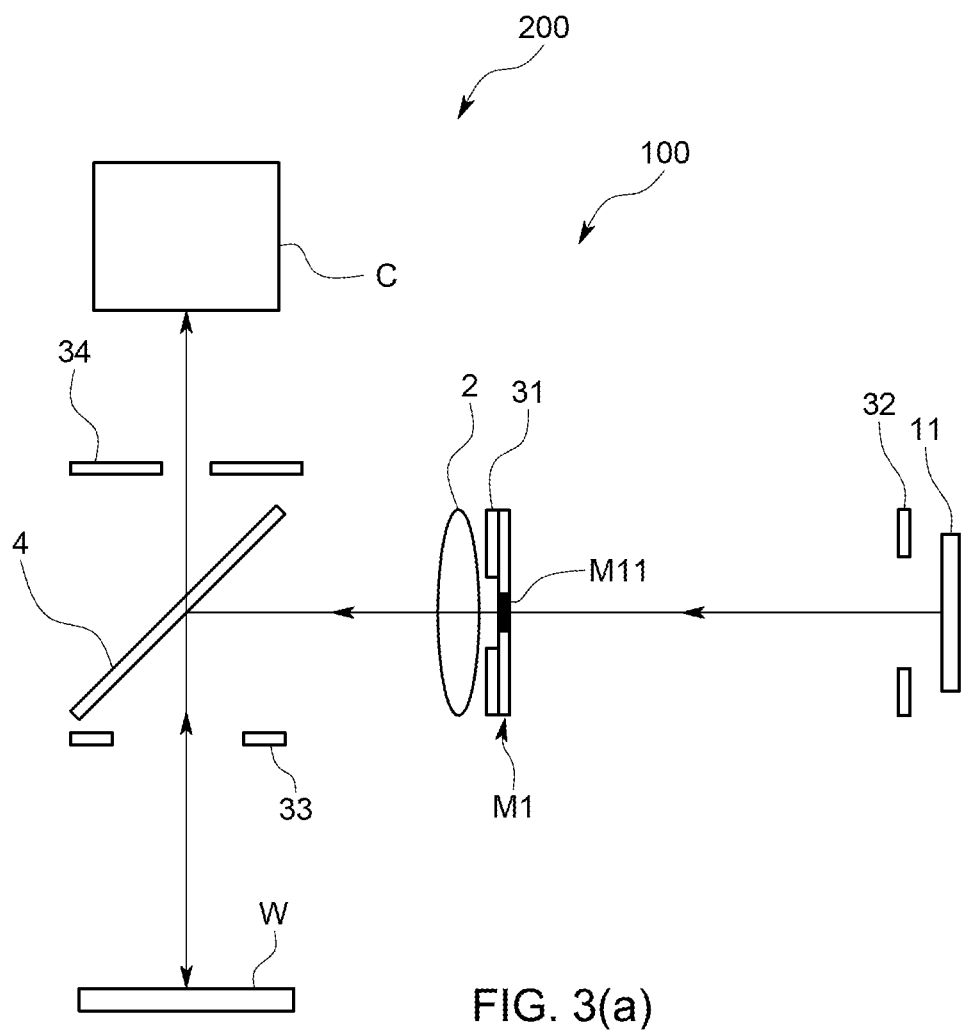
FIGS. 3(a) and 3(b) are schematic configuration diagrams of the inspection system in the same embodiment.

As illustrated in the cross-sectional view of FIG. 2 and in a simplified light path diagram of FIG. 3(a), the illumination light path L1 is formed in an L-shape, and configured to include a first light path L11 through which the inspection light travels in the horizontal direction, and a second light path L12 through which the inspection light travels downward after reflection.

In the first light path L11, the surface light source 1 that emits the inspection light, a second diaphragm 32 that is arranged near the surface light source 1, a light shielding mask M1 that is arranged near a first diaphragm 31, the first diaphragm 31 that is arranged near the light entrance side of a lens 2, the lens 2 that condenses the inspection light emitted from the surface light source 1, and a half mirror 4 that is arranged at an angle with respect to the reflection light path L2 and the illumination light path L1 so as to reflect the inspection light downward are arranged in inspection light traveling order. Further, in the second light path L12, a third diaphragm 33 through which the inspection light reflected by the half mirror 4 passes is arranged. The inspection light passing through the third diaphragm 33 from the inside of the box body 93 is applied to the inspection object W.

Also, in the reflection light path L2, the above-described third diaphragm 33, the half mirror 4, and a fourth diaphragm 34 attached on the upper surface of the box body 93 are arranged before the imaging device C in traveling order of the reflected light reflected by the inspection object W. That is, the half mirror 4 and the third diaphragm 33 are arranged in an area where the illumination light path L1 and the reflection light path L2 overlap with each other. Note that the above-described first diaphragm 31, second diaphragm 32, third diaphragm 33, and fourth diaphragm 34 are variable diaphragms, and stopping levels of the diaphragms can be appropriately changed. In addition, depending on a use mode, constant stops of which stopping levels are constant are also possible.

In the following, the arrangement and configuration of each member are described in detail.

A light emitting surface 11 of the surface light source 1 is formed of, for example, a chip-type LED or the like, in which radiation fins 12 for heat radiation are protruded outward. Also, as illustrated in the cross-sectional view of FIG. 2, the surface light source 1 is attached so as to be movable forward and backward in the first tubular body 91 in its axial direction, and adapted to be able to adjust an illumination start position of the inspection light. That is, by changing a positional relationship among the surface light source 1, the lens 2, and the inspection object W independently of the below-mentioned control of an illumination solid angle by the first diaphragm 31, an illumination range of the inspection light on the inspection object W can be controlled.

The second diaphragm 32 is arranged near the light emitting surface 11 of the surface light source 1, and by adjusting the stopping level thereof, an illumination area of the inspection light from the surface light source 1 can be changed to change the illumination range of the inspection light on the inspection object W.

Figure 3B:
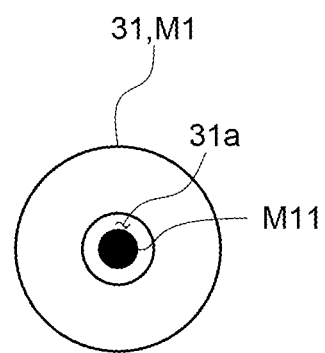

The first light shielding mask M1 is arranged close to the first diaphragm 31, and as illustrated in the schematic diagram illustrating the first diaphragm 31 and the first light shielding mask M1 as viewed along a light axis in FIG. 3(b), a circular-shaped light shielding part M11 is formed in the face plate central part of a transparent glass plate. That is, the light shielding part M11 of the first light shielding mask M1 is adapted to block a partial area of an aperture part 31a of the first diaphragm 31. The light shielding part M11 is formed so as to make the diameter thereof smaller than an aperture size of the first diaphragm 31, and adapted to block light of the inspection light emitted from the surface light source 1 passing near the light axis in the first diaphragm 31. On the other hand, the inspection light passing through the gap between the first diaphragm 31 and the light shielding part M11 enters the lens 2 and then reaches the inspection object W.

The first diaphragm 31 is arranged on the light entrance side of the lens 2, and equally adjusts illumination solid angles of the inspection light condensed by the lens 2 at respective points within the illumination range on the surface of the inspection object W. A function of controlling an illumination solid angle will be described together with the below-described action of the first light shielding mask M1.

The lens 2 is attached on a side surface opening part of the box body 93, and arranged such that an imaging plane corresponding to a position where an image of the light source is provided is positioned near the surface of the inspection object W.

The first light shielding mask M1, the first diaphragm 31, and the lens 2 as described produce the following effect. That is, depending on the positions of the first diaphragm 31 and the first light shielding mask M1 with respect to the lens 2, a tilt distribution of illumination solid angles at respective points on the imaging plane IM can also be adjusted. As in FIGS. 4(a), (b), and (c), in the case of arranging the first diaphragm 31 and the first light shielding mask M1 on the surface light source 1 side of the lens 2 and on an inner side of a focal point, an illumination solid angle having a larger outward tilt angle is formed toward the outer side of the imaging plane IM. On the other hand, in the case of arranging the first diaphragm 31 at the focal point on the surface light source 1 side, illumination directions of all illumination solid angles are parallel to the light axis, whereas in the case of arranging the first diaphragm 31 on the surface light source 1 side of the lens 2 and on the outer side of the focal point, an illumination solid angle at an outer point on the imaging plane IM has a larger tilt amount with respect to the light axis side. Note that this example describes the case where the first diaphragm 31 and the first light shielding mask M1 are arranged on the surface light source 1 side of the lens 2; however, for example, even in the case where the first diaphragm 31 and the first light shielding mask M1 are arranged on the work W side, the same effect can be produced.

Figure 4A:
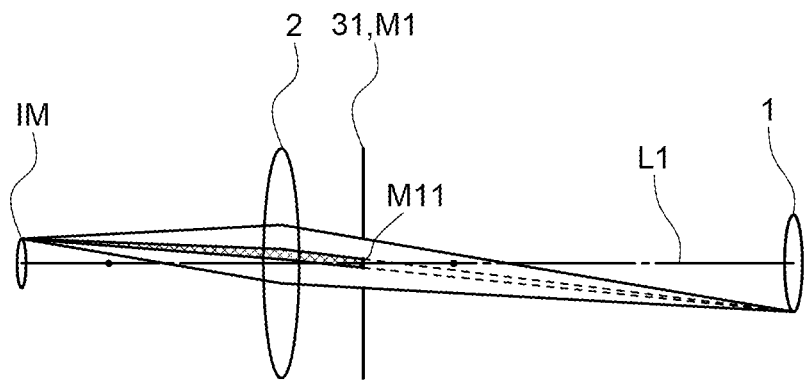
FIGS. 4(a), 4(b), and 4(c) are schematic diagrams illustrating illumination solid angles of respective points on an inspection object in the same embodiment.
Figure 4B:
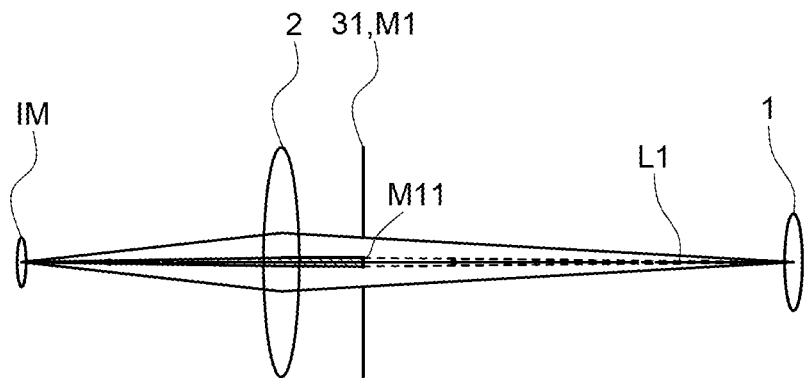
Figure 4C:
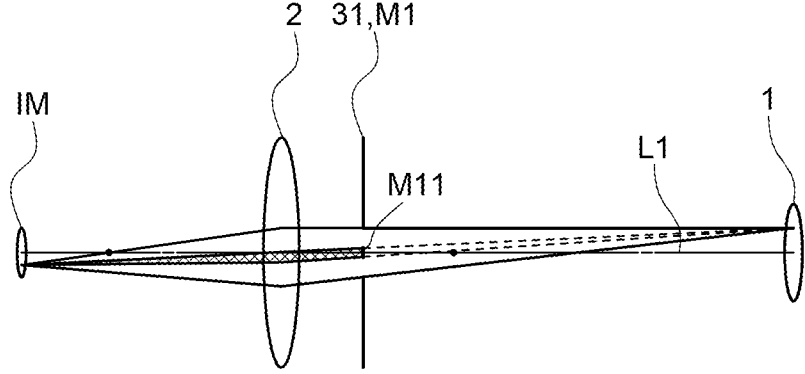

Illumination solid angles of the inspection light applied to respective points on the inspection object, which are formed by the surface light source 1, first diaphragm 31, first light shielding mask M1, and lens 2 along the illumination light path L1, are described on the basis of FIGS. 4(a), 4(b), and 4(c). Note that to simplify the descriptions, FIGS. 4(a), 4(b), and 4(c) are illustrated with the light path straightened and illustrations of the third diaphragm 33 are omitted.

FIG. 4(a) illustrates an illumination solid angle formed by light emitted from the lowermost part of the surface light source 1, FIG. 4(b) illustrates an illumination solid angle formed by light emitted from the central part of the surface light source 1, and FIG. 4(c) illustrates an illumination solid angle formed by light emitted from the upper side of the surface light source 1. As is clear from FIGS. 4(a), 4(b), and 4(c), even in the case where the first light shielding mask M1 is present near the first diaphragm 31, a shadow is not formed on the imaging plane IM on the inspection object W, but the reduced image of the surface light source 1 in accordance with the lens equation is provided.

Also, the surface light source 1 and the lens 2 are arranged with respect to the inspection object W so as to provide the image of the surface light source 1 on the inspection object W, and therefore by arranging the first diaphragm 31 on the way to the inspection object W, sizes of illumination solid angles at respective points on the imaging plane IM can be changed to be uniform. In other words, at all points on the imaging plane IM, illumination solid angles have substantially the same size, and increasing the stopping level of the first diaphragm 31 can decrease an illumination solid angle, whereas decreasing the stopping level of the first diaphragm 31 can increase an illumination solid angle.

Further, in the present embodiment, since the first light shielding mask M1 is arranged near the first diaphragm 31, a dark domain can be formed within a part of an illumination solid angle. In the present embodiment, since the first light shielding mask M1 is formed with the light shielding part M11 so as to shield light near the light axis, as illustrated in the respective diagrams of FIGS. 4(a), 4(b), and 4(c), substantially thin conical-shaped dark domains are formed in the central parts of illumination solid angles at respective points on the imaging plane IM. In other words, an illumination solid angle is formed in a shape where a thin conical-shaped dark domain fits into a hollow part of a hollow conical-shaped light domain.

Changing the stopping level of the first diaphragm 31 can mainly adjust the size of the outer circumference of the light domain, i.e., the size of the whole of the illumination solid angle, whereas adjusting the size of the light shielding part M11 of the first light shielding mask M can adjust the size of the dark domain. As described, the present embodiment can freely control the size of an illumination solid angle of the inspection light applied to each point on the inspection object W using the first diaphragm 31 as well as freely set the size, shape, or position of a dark domain within an illumination solid angle on the basis of the size, shape, or position of the light shielding part M11 of the first light shielding mask M1.

The half mirror 4 is a circular-shaped thin mirror supported by a substantially square-shaped frame body 41. Using such a half mirror 4 makes it possible to form a part of the mirror 4 where the reflection or transmission takes place to be thin, and thereby minimize an imaging error due to minute refraction or the like taking place when the reflected light from the inspection object W is transmitted through the half mirror 4.

The third diaphragm 33 is attached on a lower surface opening part of the box body 93, and arranged between the half mirror 4 and the inspection object W. The third diaphragm 33 can more finely adjust an illumination solid angle determined by the first diaphragm 31. Also, the third diaphragm 33 can prevent stray light, which is produced when the inspection light having passed through the third diaphragm 33 is reflected by the inspection object W to become the reflected light, from intruding into the inspection illumination device.

The fourth diaphragm 34 is attached on an upper surface opening part of the box body 93, and arranged between the half mirror 4 and the imaging device C. The fourth diaphragm 34 is used for further adjusting an observation solid angle at which the reflected light entering the imaging device C is observed. Also, the second tubular body 92 is telescopically attached, and thereby adapted to be able to adjust a separation distance between the fourth diaphragm 34 and the imaging device C. This makes it possible to further accurately optimize an intensity profile based on a variation in tilt of the reflected light.

The reason why the imaging apparatus C can easily detect a minute defect or the like as a contrast when using the inspection illumination device 100 configured as described above is described with reference to FIGS. 5(a) and 5(b) and 6(a) and 6(b).

For example, the third diaphragm 33 can accurately coaxially make a dark domain of an illumination solid angle and the observation solid angle equal in size to each other. Since the present embodiment relates to the coaxial illumination, in the case where there is no defect, a dark domain of an illumination solid angle and a dark domain of a reflected light solid angle completely coincide with each other, and therefore, in the case where the third diaphragm 33 makes the observation solid angle of the imaging device C equal in size to the dark domain of the illumination solid angle, as illustrated in FIG. 5(a), the dark domain of the illumination solid angle of the reflected light and the observation solid angle completely coincide with each other.

In this case, since a light domain is normally absent within the observation solid angle as in FIG. 5(a), only a dark picture image is taken, whereas as illustrated in FIG. 5(b), in the case where the inspection object W has a defect and thereby a tilt variation in reflected light solid angle occurs, a light domain partially moves into the observation solid angle as in FIG. 5(b), and therefore a light picture image is taken. That is, the tilt variation in reflected light solid angle can be detected as observation light intensity information observed by the imaging device C, and thereby the defect can be detected.

Figure 6A:
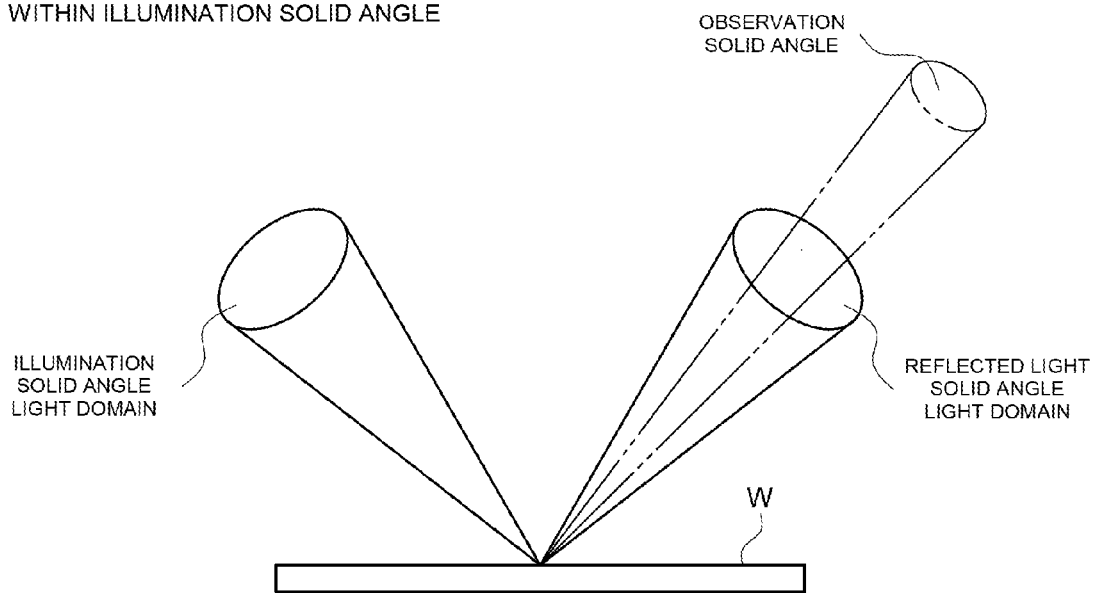
FIGS. 6(a) and 6(b) are schematic diagrams illustrating the reason why a conventional inspection system cannot detect a minute defect.
Figure 6B:
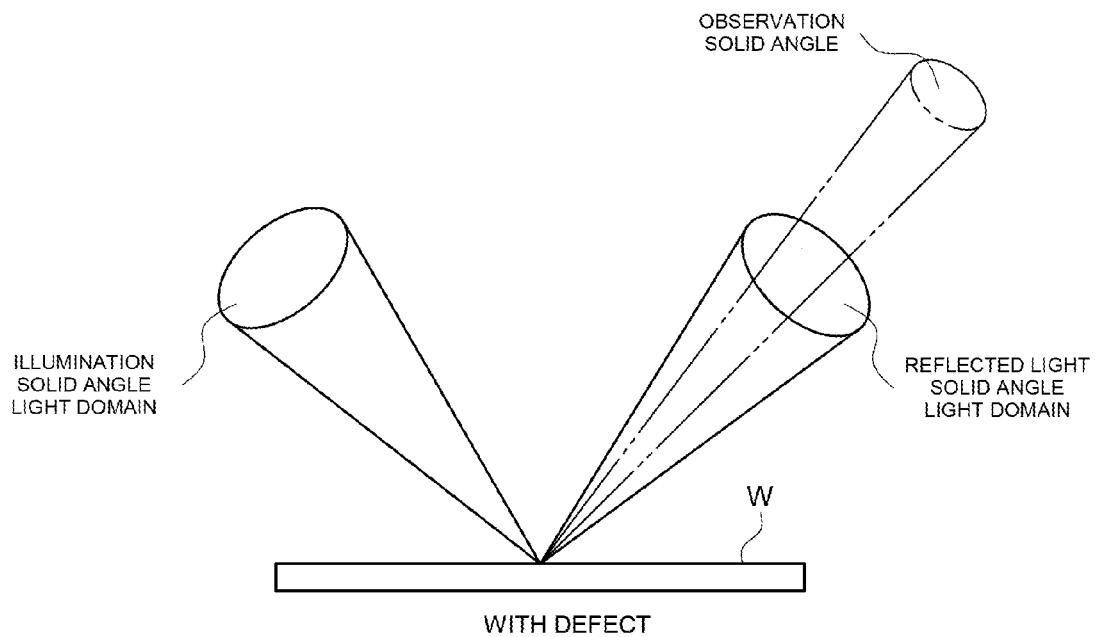

On the other hand, in the case where the first light shielding mask M1 is not arranged, even in the case where an equivalent tilt variation in reflected light solid angle occurs as illustrated in FIGS. 6(a) and 6(b), a light amount does not change at all considering the inside of the observation solid angle as illustrated in FIG. 6(b), and therefore even the imaging device C cannot detect a change in intensity information. For this reason, a minute defect cannot be detected.

Further, by adjusting the size of an illumination solid angle using the first diaphragm 31 or optimizing the size of the light shielding part M11 of the first light shielding mask M1 depending on a characteristic of a defect or the like, more accurate defect detection can be performed.

As described, the inspection system 200 of the present embodiment can accurately control the size of an illumination solid angle at each point within the entire inspection light illumination range on the inspection object W by forming an imaging optical system and then providing the first diaphragm 31.

In addition, the first light shielding mask M1 arranged near the first diaphragm 31 can form a dark domain within an illumination solid angle without forming a shade on the imaging plane IM on the inspection object W. Further, since the size of an illumination solid angle can be changed and also a dark domain is present inside an illumination solid angle, a mode that can easily change a light amount within the observation solid angle depending on whether or not a defect is present can be made, and therefore a defect or the like that has been undetectable in the past can be detected.

In other words, the inspection system 200 of the present embodiment can freely set an inclusion relationship between a reflected light solid angle and the observation solid angle to a relationship suitable for defect detection by adjusting the size of an illumination solid angle, the shape of a dark domain, or the like, and can therefore make even a defect or the like, which has been difficult to detect in the past, appear as intensity information on an imaged picture image to detect the defect.

Next, another embodiment of the present invention is described.

Figure 7A:
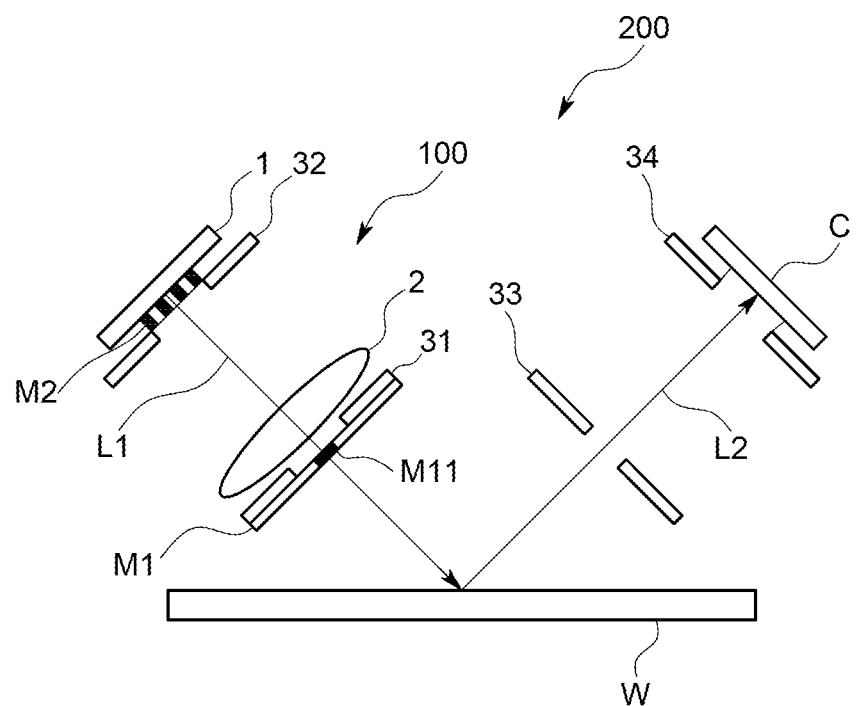
FIGS. 7(a) and 7(b) are schematic diagrams illustrating an inspection system according to another embodiment of the present invention.

In the above-described embodiment, the inspection system 200 is configured on the basis of the coaxial illumination; however, an inspection system 200 may be configured using a simple optical system that, as illustrated in FIG. 7(a), applies inspection light to an inspection object obliquely from above, and picture images the inspection object W by an imaging device C with use of reflected light of the inspection light to perform inspection. Further, as illustrated in FIG. 7(a), a first diaphragm 31 and a first light shielding mask M1 may be arranged between a lens 2 and the inspection object W.

Also, as illustrated in FIG. 7(a), shape accuracy of the inspection object W may be made inspectable by providing not only the first light shielding mask M1 near the first diaphragm 31 but further providing a second light shielding mask M2 near a surface light source 1.

Figure 7B:
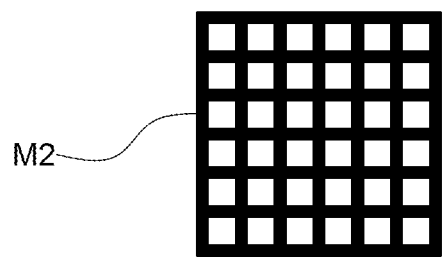

More specifically, the second light shielding mask M2 is formed with, for example, as illustrated in FIG. 7(b), a grid-like light shielding part M21, and forms a grid-like light and dark part on the inspection object W. In the case where the shape of the inspection object W deviates from a normal shape, a distortion amount of the grid on an imaging plane IM of the inspection light on the inspection object W changes, and thereby a shape error or the like can be detected. Also, in the second embodiment as well, an inclusion relationship between a reflected light solid angle and an observation solid angle can be well adjusted by the first diaphragm 31, the shape of a light shielding part M11 of the first light shielding mask M1, and the like, and therefore even subtle grid distortion can be detected as contrast in an imaged picture image. Accordingly, the shape error or the like of the inspection object W can be detected with high accuracy.

Next, still another embodiment of the present invention is described.

In the above-described embodiments, the case where an illumination solid angle and a dark domain of the illumination solid angle are formed in a conical shape of which a bottom surface is circular-shaped is described; however, an illumination solid angle having a different shape or size can be set by the first diaphragm 31 and the shape of the light shielding part M11 of the first light shielding mask M1.

Figure 8A:
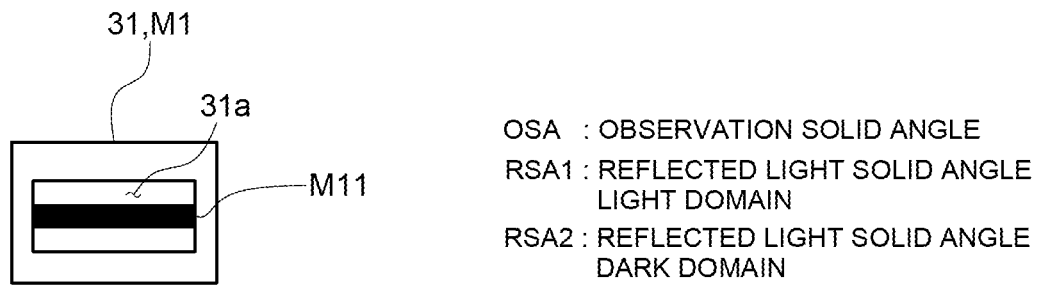
FIGS. 8(a), 8(b), 8(c), and 8(d) are schematic diagrams illustrating a defect detection principle in an inspection system according to still another embodiment of the present invention.
Figures 8B, 8C, 8D:
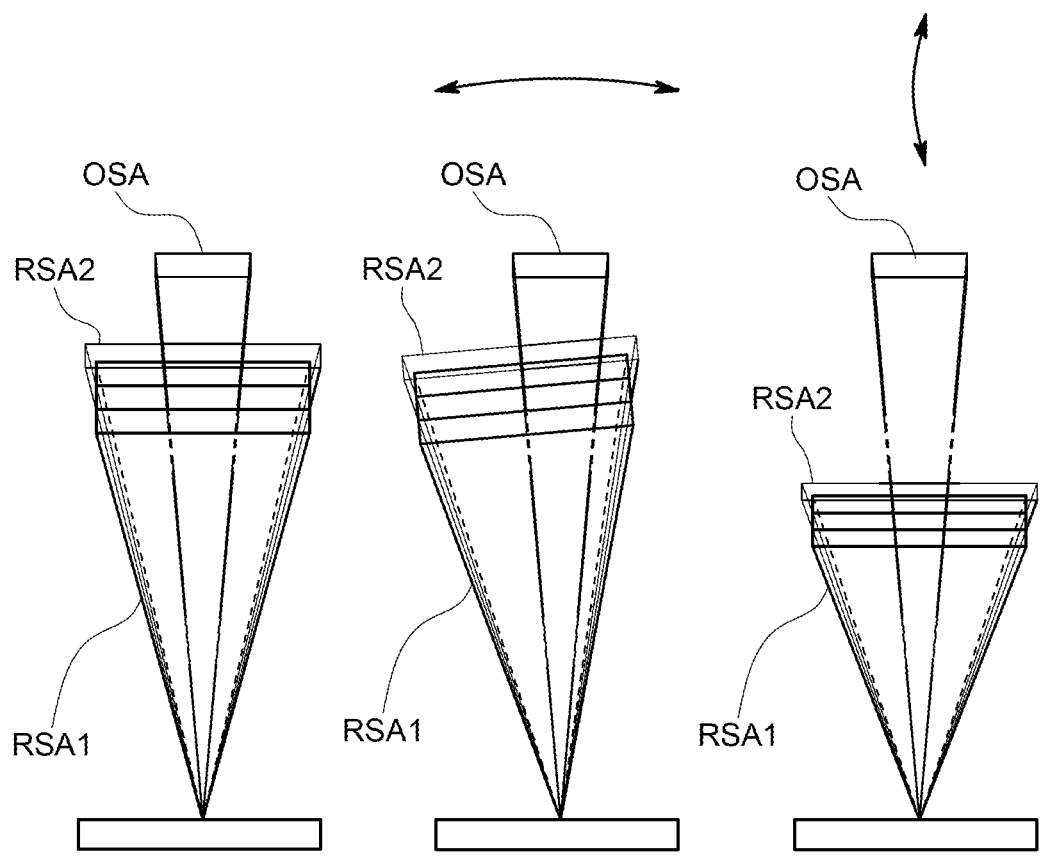

In this embodiment, as illustrated in FIG. 8(a), an aperture part 31a of a first diaphragm 31 is formed in a substantially rectangular shape, and a light shielding part M11 of a first light shielding mask M1 is also formed in a rectangular shape smaller than the aperture part 31a. In addition, an observation solid angle is also formed as a quadrangular pyramid that is smaller than a dark domain of an illumination solid angle and has a rectangular-shaped bottom surface. Specifically, depending on a diaphragm position, stopping shape, or the shape of size of the light shielding part M11 of the first light shielding mask arranged on an aperture part of the diaphragm in an imaging optical system including an imaging device C, an arbitrary observation solid angle as illustrated in FIGS. 8(b), 8(c), and 8(d) can be formed. Details of a method for forming an observation solid angle in terms of shape or size are the same as a method for forming an illumination solid angle in terms of shape or size, or a method for forming a dark domain, and therefore omitted.

As in this embodiment, in the case of forming an illumination solid angle as a pyramid of which the bottom surface is rectangular-shaped, and a dark domain as a pyramid of which the bottom surface is rectangular-shaped as well, a reflected light solid angle is also formed as a pyramid of which the bottom surface is rectangular-shaped. Accordingly, in FIGS. 8(b), 8(c), and 8(d), illustration of an illumination solid angle is omitted, and only a reflected light solid angle is illustrated.

As illustrated in FIG. 8(b), a configuration adapted to form the observation solid angle within a dark domain of a reflected light solid angle normally makes it possible to effectively detect a defect making a tilt of reflected light have directionality.

More specifically, as illustrated in FIG. 8(c), in the case of a defect that tilts a reflection direction in a long side direction of a rectangular shape, the observation solid angle is unlikely to be out of a dark domain of a reflected light solid angle, and therefore no change occurs with a dark picture image taken, resulting in no detection.

On the other hand, as illustrated in FIG. 8(d), in the case of a defect that tilts a reflection direction tilt in a short side direction of a rectangular shape, even a small change amount causes the observation solid angle to be out of a dark domain of a reflected light solid angle, and therefore a light picture image is taken, resulting in detection.

As described, in the case where it is desired to detect only a specific defect that causes a tilt of a reflection direction to have directionality, as illustrated in FIGS. 8(a)-(d), it is only necessary to form the shapes of an illumination solid angle and a dark domain to be long only in one direction, and make short side directions coincide with each other so as to coincide with the directionality caused by the defect desired to be detected.

In addition, for example, the first diaphragm 31 and the first light shielding mask M1 may be configured to be rotatable around a light axis, and directions of an illumination solid angle and a dark domain on an inspection object W may be made to coincide with directionality of a tilt of reflected light from a defect. Further, not only inspection light of which an illumination solid angle and a dark domain respectively have rectangular-shaped bottom surfaces is formed as described in this embodiment, but also inspection light of which an illumination solid angle has, for example, an elliptically-shaped bottom surface may be applied.

A different embodiment is described.

This embodiment is configured to have a structure with multiple hollows by forming multiple dark domains within an illumination solid angle, and thereby able to detect only a defect having a characteristic that tilts reflected light in a specific direction by a specific angle.

Figure 9A:
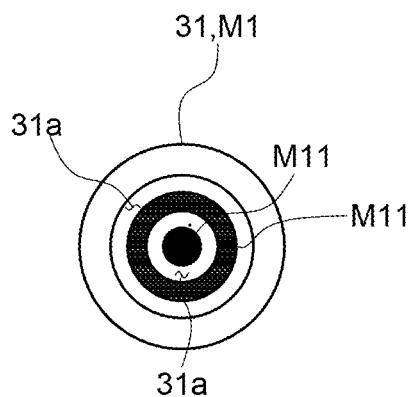
FIGS. 9(a), 9(b), 9(c), and 9(d) are schematic diagrams illustrating a defect detection principle in an inspection system according to a different embodiment of the present invention.
Figure 9B:
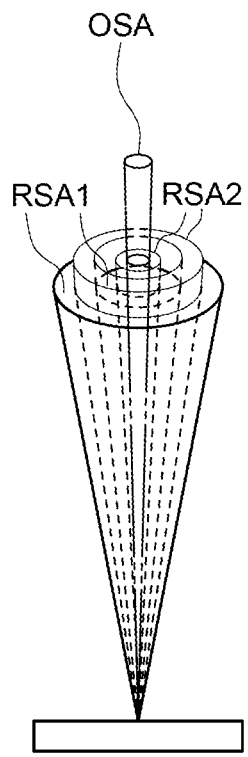

Specifically, as illustrated in FIG. 9(a), multiple light shielding parts M11 of a first light shielding mask M1 are concentrically formed, and a dark domain and a light domain of an illumination solid angle are alternately formed from the inner side to the outer side. Also, as illustrated in FIG. 9(b), an observation solid angle is formed so as to be thinner than the width of a light domain between a dark domain formed in the central part of a reflected light solid angle and a dark domain formed on the outer side of the dark domain.

Figure 9C:
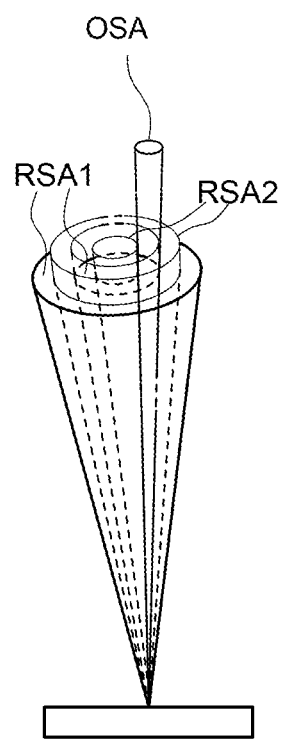
Figure 9D:
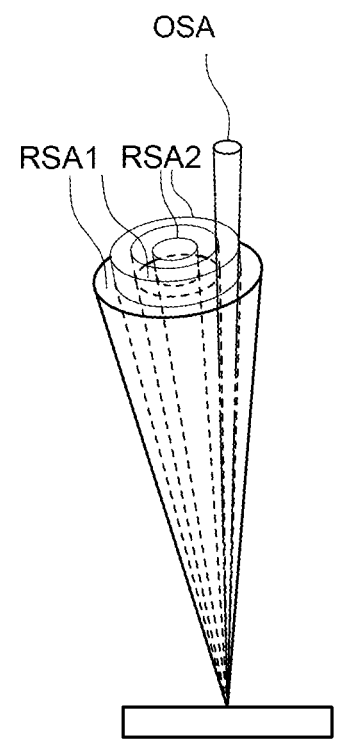

In doing so, as illustrated in FIG. 9(c), in the case where a reflected light solid angle is subtly tilted by a defect, a light domain of the reflected light solid angle moves into the observation solid angle, and therefore a light picture image is taken, making it possible to detect the defect. On the other hand, as illustrated in FIG. 9(d), in the case where a reflected light solid angle is greatly changed by a defect, an outer dark domain again moves into the observation solid angle, and therefore a dark picture image is taken, and the defect is not detected.

That is, by forming multiple dark domains as in this embodiment, among defects, only defects that tilt a reflected light solid angle at predetermined angles can be detected. Also, for example, in the case where an inspection object has two different inspection object surfaces including a horizontal surface in the central part and a continuously formed tilted surface annularly surrounding the outer circumference of the horizontal surface, the amount of change in reflection direction caused by the difference in tilt between the respective surfaces can be prevented from being detected by performing setting such that an observation solid angle is included in an outer dark domain. Also, a change in reflection direction caused by a defect on the horizontal surface can be easily determined by making an adjustment such that the observation solid angle is included in an inner light domain, and making an adjustment such that an outer light domain moves into the observation solid angle only in the case where a change caused by the tilted surface and a change caused by a defect on the tilted surface are combined, even in the case where tilts of the respective surfaces are different.

An embodiment for further improving inspection accuracy in the case where inspection light must be applied to an inspection object W, for example, obliquely from above without use of coaxial illumination due to various restrictions or the like is described.

Figure 10A:
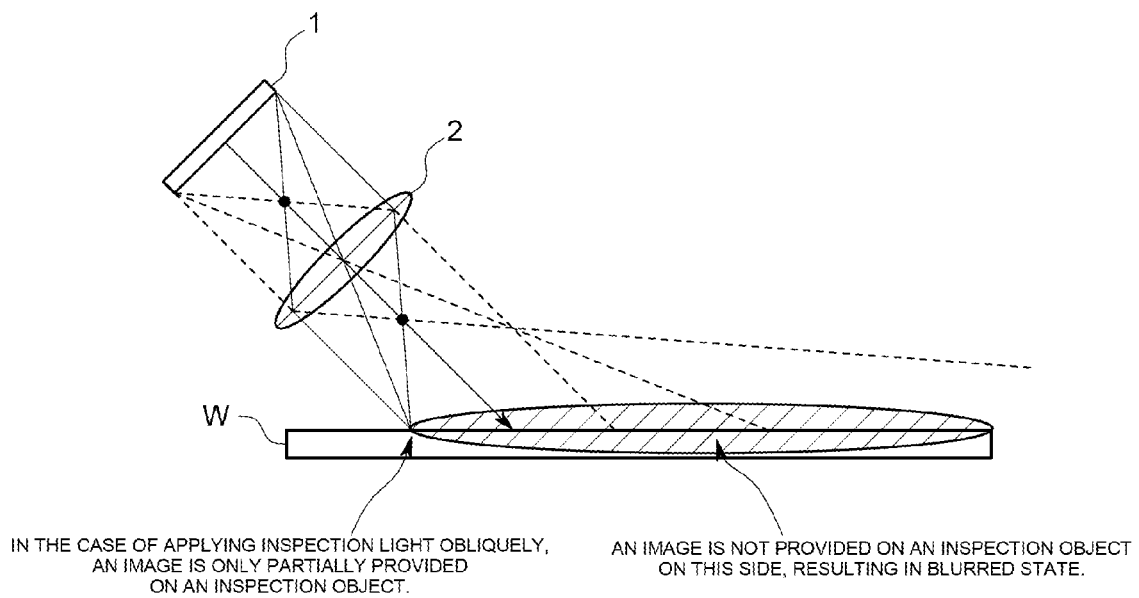
FIGS. 10(a), and 10(b) are schematic diagrams illustrating an inspection illumination device according to a further different embodiment of the present invention.

As illustrated in FIG. 10(a), in the case where a light axis of a lens 2 is oblique to an inspection object plane Wa of an inspection object W, and inspection light is applied to the inspection object plane Wa obliquely from above, and in the case where a light emitting plane 1a of a surface light source 1 is arranged in parallel to a principal plane 2a of the lens 2, the image of the surface light source 1 can be partially provided on the inspection object plane Wa, but the rest of the image is displaced from an imaging position, and therefore an imaging plane is blurred.

That is, in the case where the principal plane 2a of the lens 2 is in parallel to the inspection object plane Wa as in coaxial illumination, the image of the surface light source 1 can be completely provided, and the shapes and sizes of illumination solid angles can be made uniform; however, in the case of applying the inspection light obliquely from above, the shapes and sizes of illumination solid angles of the inspection light may be changed in a partial area and affect inspection accuracy.

Figure 10B:
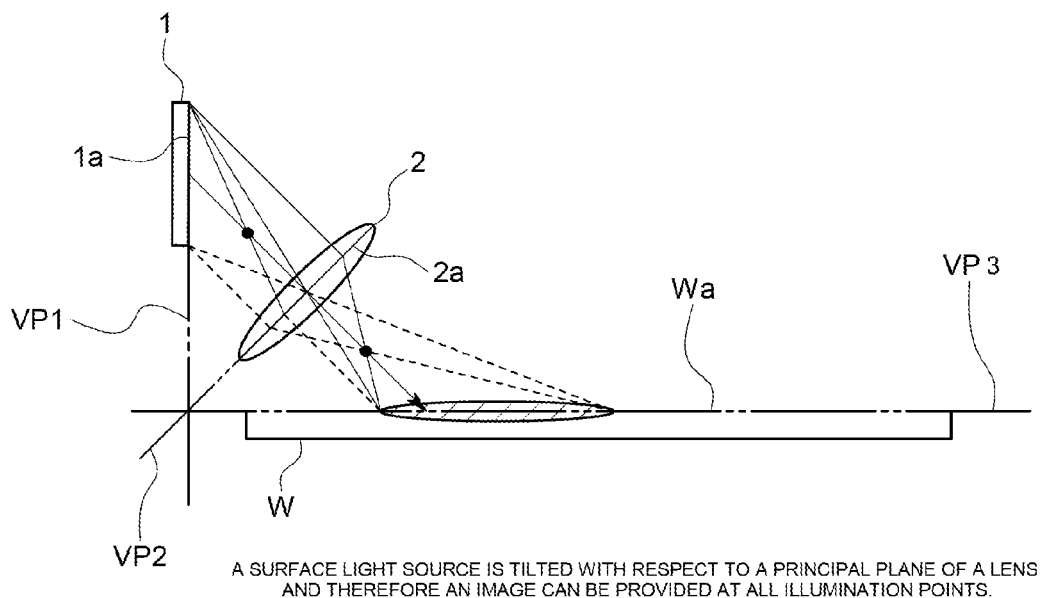

In order to solve such a problem, in this embodiment, as illustrated in FIG. 10(b), the light emitting plane 1a of the surface light source 1 is arranged not in parallel to the principal plane 2a of the lens, but at an angle with respect to the principal plane 2a. More specifically, a first virtual plane VP1 including the light emitting plane 1a, a second virtual plane VP2 including the principal plane 2a of the lens, and a third virtual plane VP3 including the inspection object plane Wa are arranged so as to intersect with one another on one straight line.

Next, a method for adjusting a tilt of the light emitting plane 1a of the surface light source 1 is described. Note that the surface light source 1 is arranged with an attitude adjustment mechanism for changing a separation distance to the lens 2 along the light axis as well as changing a tilt state with respect to the principal plane 1a.

First, the center of the light emitting plane 1a of the surface light source 1 is arranged on the light axis of the lens 2, and respective separation distances among the surface light source 1, the lens 2, and the inspection object W are set so as to provide an image of the center of the light emitting plane 1a on the inspection object plane Wa.

Then, an intersection line between the inspection object plane Wa of the inspection object W and the principal plane 2a of the lens 2 is obtained, and a plane intersecting with the intersection line and the center of the light emitting plane 1a is defined as the first virtual plane VP1. By adjusting the tilt of the surface light source 1 so as to make the first virtual plane VP1 and the light emitting plane 1a coincide with each other, a state as in FIG. 10(b) is formed. As described, by setting the tilt of the surface light source 1, separation distances meeting the Gaussian formula are set between respective points on the light emitting surface 1a and corresponding points on the inspection object plane Wa, and therefore the image of the entire light emitting plane 1a of the surface light source 1 can be provided on the inspection object plane Wa.

By arranging the surface light source 1 as described, separation distances can be adjusted so as to meet the Gaussian formula between respective points on the light emitting plane 1a of the surface light source 1 and corresponding points on the inspection object plane Wa of the inspection object W.

Accordingly, in the case of FIG. 10(b), the image of the surface light source 1 is uniformly provided on the inspection object plane Wa, and the sizes and shapes of illumination solid angles and those of dark domains of the illumination solid angles can be made uniform to increase inspection accuracy.

Next, a configuration for increasing inspection accuracy in the case where an inspection object W has an inspection object curved surface Wb is described. In the case where the inspection object W has the inspection object curved surface Wb, to which a surface light source 1 having a light emitting plane 1a applies inspection light, the image of the surface light source 1 can be provided on a part of the inspection object curved surface Wb, but on the rest of the curved surface Wb, cannot be provided because separation distances from a lens are different.

In order to make it possible to apply inspection light emitted from the surface light source 1 in a preferable mode to provide the image of the inspection light at all points on such a curved surface, it is only necessary that the surface light source 1 has a light emitting curved surface 1b, and the shape of the light emitting curved surface 1b is set such that the image of the lights emitted from respective points on the light emitting curved surface 1b are provided at respective corresponding points on the inspection object curved surface Wb through the lens.

Figure 11A:
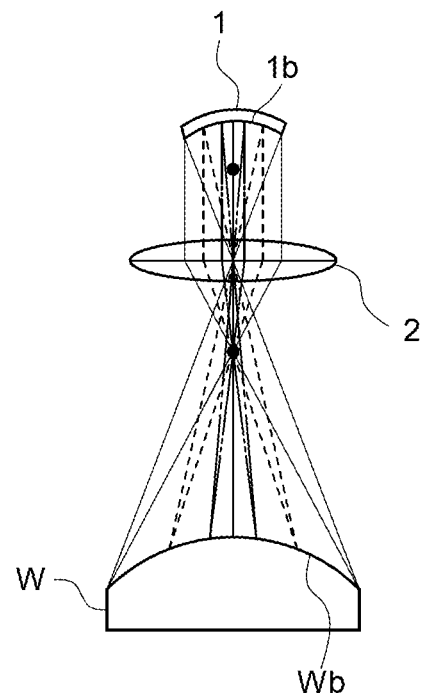
FIGS. 11(a) and 11(b) are schematic diagrams illustrating variations of the present invention.

More specifically, as illustrated in FIG. 11(a), in the case of illumination in a mode where a light axis of the lens 2 and the central axis of the inspection object W coincide with each other, for example, it is only necessary that the shape of the light emitting curved surface 1b is substantially similar to the inspection object curved surface Wb.

In other words, it is only necessary to determine the shape or curvature of the light emitting curved surface 1b so as to meet the Gaussian formula between respective points on the inspection object curved surface Wb and respective corresponding points on the light emitting curved surface 1b.

Figure 11B:
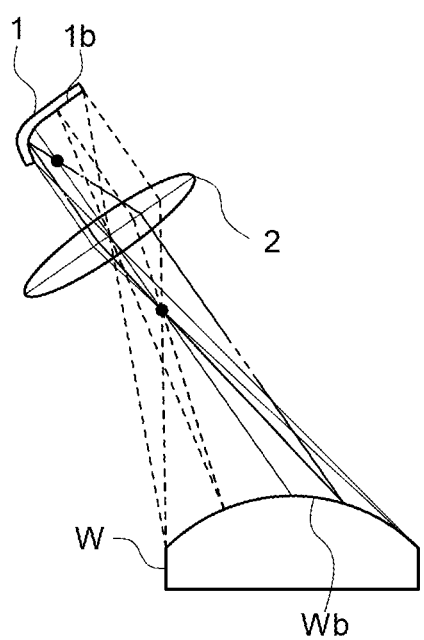

Also, as illustrated in FIG. 11(b), in the case of applying inspection light obliquely from above as well, by using the same approach, the shape of a corresponding light emitting curved surface 1b can be set.

Other embodiments are described.

In each of the above-described embodiments, the shape of the light shielding part of the first light shielding mask is circular-shaped, but the light shielding part may be variously shaped, such as a polygonal shape such as a triangular shape or a rectangular shape, or a grid-like shape. In short, it is only necessary that the light shielding part forms a dark domain within an illumination solid angle and is smaller than the aperture size of the first diaphragm so as not to block the entire inspection light. Also, the shape or size of an observation solid angle based on a configuration of an imaging optical system is also arbitrarily set in the same manner. Further, by selecting a combination of an illumination solid angle and an observation solid angle respectively having arbitrary shapes depending on the character or the like of a defect, more accurate defect inspection becomes possible.

The shape of the light shielding part of the second light shielding mask is also not limited to that in the embodiment, but may be another shape. For example, various shapes such as a striped shape, a circular shape, and a polygonal shape are also possible.

A method for setting an observation solid angle is not limited to that described in each embodiment, and it is necessary to appropriately set an observation solid angle on the basis of a dark domain of an illumination solid angle. For example, an observation solid angle may be configured to normally include a light domain of a reflected light solid angle, and allow a dark domain to move thereinto according to a change in tilt caused by a defect.

In the above-described embodiments, the first light shielding mask is arranged close to the first diaphragm, but it is only necessary that the first light shielding mask is arranged near the first diaphragm, and both of them may be separated from each other to a certain extent. Also, the imaging plane of the surface light source is only required to be near an inspection object, and the image of the surface light source is not required to be provided strictly on the inspection object.

Besides, the various variations and embodiments may be combined without departing from the scope of the present invention.

INDUSTRIAL APPLICABILITY

According to the present invention, an inspection system for detecting a defect, a flaw, or the like of a product through machine vision can be arranged.

The invention claimed is:
1. An inspection system including: an inspection illumination device that applies inspection light to an inspection object; and an imaging device that images light reflected or scattered at the inspection object, wherein
   the inspection illumination device comprises:
     a surface light source that emits the inspection light;
     a lens that is arranged between the surface light source and the inspection object, and provides an image of the surface light source near the inspection object; and a first light shielding mask that is arranged between the surface light source and the inspection object, and forms a dark domain within an illumination solid angle of the inspection light applied to each point on the inspection object; and the imaging device has an observation solid angle, wherein a shape or a size of the observation solid angle is set on a basis of a shape or a size of a dark domain within the illumination solid angle of the inspection light applied from the inspection illumination device to each point on the inspection object.

2. The inspection system according to claim 1, wherein the size of the observation solid angle is set substantially equal to the size of the dark domain of the illumination solid angle.

3. The inspection system according to claim 1, further comprising a first diaphragm that is arranged at a predetermined position with respect to a focal point of the lens.

4. The inspection system according to claim 3, wherein the first light shielding mask is arranged near the first diaphragm, and a light shielding part of the first light shielding mask is formed to be smaller than an aperture size of the first diaphragm.

5. The inspection system according to claim 1, wherein a second light shielding mask formed with a predetermined mask pattern is arranged near an emission side of the surface light source.

6. The inspection system according to claim 1, wherein:

the surface light source has a light emitting plane;

a light axis of the lens is arranged obliquely to an inspection object plane on the inspection object; and a first virtual plane including the light emitting plane, a second virtual plane including a principal plane of the lens, and a third virtual plane including the inspection object plane intersect on one straight line.

7. The inspection system according to claim 1, wherein:

the surface light source has a light emitting curved surface; and a shape of the light emitting curved surface is set such that light emitted from each point on the light emitting curved surface is imaged at each point on an inspection object curved surface through the lens.

8. An inspection illumination device comprising:

a surface light source that emits inspection light;

a lens that is arranged between the surface light source and an inspection object, and provides an image of the surface light source near the inspection object; and a first light shielding mask that is arranged between the surface light source and the inspection object, and forms a dark domain within the illumination solid angle of the inspection light applied to each point on the inspection object.

* * * * *